(12) United States Patent
George et al.

(10) Patent No.: US 7,579,555 B2
(45) Date of Patent: Aug. 25, 2009

(54) RF SHIELDING COVER FOR RF RADIATING APPLICATOR

(75) Inventors: Frank R. George, Scottsdale, AZ (US); Robert T. Bryant, Tempe, AZ (US); Michael F. Daly, Phoenix, AZ (US); Arthur A. Loya, Mesa, AZ (US); Mary C. Ritz, Scottsdale, AZ (US)

(73) Assignee: Regenesis Biomedical, Inc., Scottsdale, AZ (US)

( * ) Notice: Subject to any disclaimer, the term of this patent is extended or adjusted under 35 U.S.C. 154(b) by 86 days.

(21) Appl. No.: 11/272,983

(22) Filed: Nov. 14, 2005

(65) Prior Publication Data
US 2008/0093119 A1    Apr. 24, 2008

Related U.S. Application Data

(63) Continuation of application No. 11/202,728, filed on Aug. 11, 2005, which is a continuation of application No. 09/661,604, filed on Sep. 14, 2000, now Pat. No. 6,974,961.

(60) Provisional application No. 60/154,435, filed on Sep. 17, 1999.

(51) Int. Cl.
    *H05K 9/00*    (2006.01)
(52) U.S. Cl. .................. 174/378; 174/382; 607/115
(58) Field of Classification Search .............. 174/35 R, 174/35 MS, 378, 382, 388, 390; 361/816, 361/818, 800; 607/115
See application file for complete search history.

(56) References Cited

U.S. PATENT DOCUMENTS

| | | | |
|---|---|---|---|
| 3,918,458 A | * | 11/1975 | Nethery ...................... 607/104 |
| 3,942,023 A | | 3/1976 | Flaugnatti .................... 250/515 |
| 4,605,124 A | | 8/1986 | Sandel et al. ............... 206/223 |
| 4,715,366 A | | 12/1987 | Teeple ..................... 128/132 D |
| 4,980,564 A | | 12/1990 | Steelmon ................. 250/505.1 |

(Continued)

FOREIGN PATENT DOCUMENTS

GB    2193099 A    2/1988

(Continued)

OTHER PUBLICATIONS

International Search Report mailed Apr. 25, 2001, for PCT Application No. PCT/US00/40903 filed Sep. 14, 2000, 8 pages.

Japanese Office Action mailed Aug. 12, 2008 for Japanese Application No. 2001-522914, 4 pages (English translation attached, 5 pages).

*Primary Examiner*—Hung V Ngo
(74) *Attorney, Agent, or Firm*—Morrison & Foerster LLP

(57) ABSTRACT

A disposable cover for electromagnetic treatment applicators prevents undesired exposure to potentially harmful radiation. The cover is a pouch-like structure having a back surface constructed from RF shielding material, such as metallized polyethylene, which back surface faces opposite, or away from, the treatment area. A portion of the cover which faces the treatment area is constructed from material transmissive to RF radiation from the applicator. Securing means, such as adhesive strips, or interlocking edges close an open end to secure the applicator inside the cover and to prevent RF radiation through the closed end. In use, an applicator is inserted within the cover and positioned over the area to be treated with the RF transmissive material overlying the treatment area. When the applicator is activated, the generated electromagnetic energy exits the cover only through the RF transmissive material to the treatment area and the RF shielding material prevents exposure of the caregiver to potentially harmful radiation.

19 Claims, 2 Drawing Sheets

U.S. PATENT DOCUMENTS

| | | | |
|---|---|---|---|
| 5,073,984 A | 12/1991 | Tone et al. | 2/2 |
| 5,115,140 A | 5/1992 | Rodriguez | 250/516.1 |
| 5,220,175 A | 6/1993 | Cole | 250/515.1 |
| 5,247,182 A | 9/1993 | Servant et al. | 250/516.1 |
| 5,336,896 A | 8/1994 | Katz | 250/515.1 |
| 5,456,698 A | 10/1995 | Byland et al. | 607/36 |
| 5,523,581 A | 6/1996 | Cadwalader | 250/515.1 |
| 5,548,125 A | 8/1996 | Sandbank | 250/519.1 |
| 5,597,979 A * | 1/1997 | Courtney et al. | 174/35 R |
| 5,720,770 A | 2/1998 | Nappholz et al. | 607/30 |
| 5,739,463 A | 4/1998 | Diaz et al. | 174/35 R |
| 5,861,019 A | 1/1999 | Sun et al. | 607/60 |
| 5,989,229 A * | 11/1999 | Chiappetta | 604/263 |
| 6,325,538 B1 | 12/2001 | Heesch | 378/203 |
| 6,456,256 B1 | 9/2002 | Amundson et al. | 343/873 |
| 6,481,888 B1 | 11/2002 | Morgan | 378/204 |
| 6,708,065 B2 | 3/2004 | Von Arx et al. | 607/60 |
| 6,967,281 B2 | 11/2005 | George et al. | |
| 6,974,961 B1 | 12/2005 | George et al. | |
| 7,331,463 B2 * | 2/2008 | Hickey | 206/570 |
| 2003/0233063 A1 * | 12/2003 | Nakatani | 604/2 |
| 2005/0269219 A1 * | 12/2005 | Discko, Jr. | 206/219 |
| 2006/0113102 A1 | 6/2006 | George et al. | |

FOREIGN PATENT DOCUMENTS

| | | |
|---|---|---|
| JP | 62-258680 A | 11/1987 |
| JP | 6-57266 B2 | 8/1994 |
| JP | 11-342211 A | 12/1999 |
| WO | WO 95/26780 | 10/1995 |

* cited by examiner

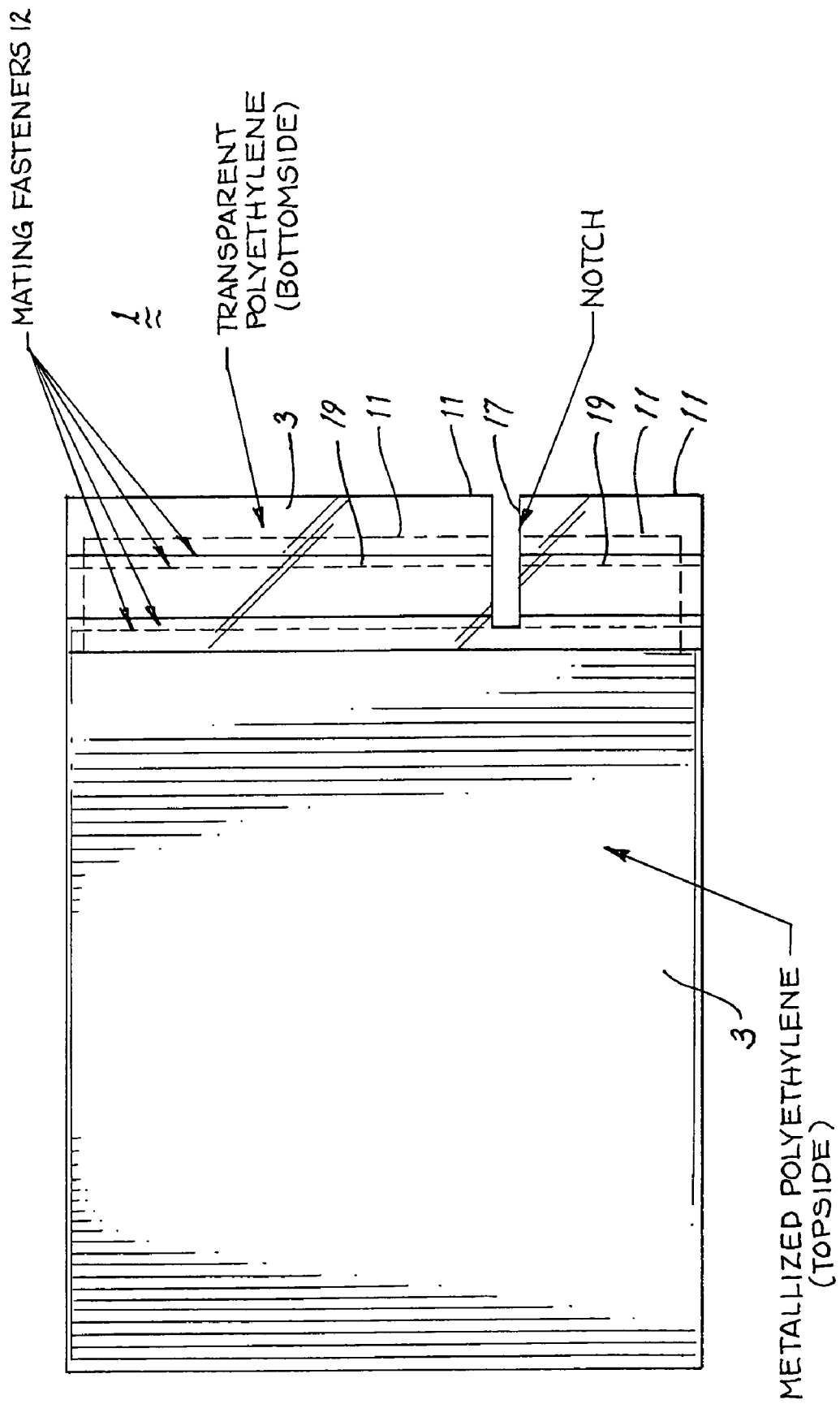

RF SHIELDING COVER FOR RF RADIATING APPLICATOR

CROSS REFERENCE TO RELATED APPLICATIONS

This application is a continuation application of an application entitled "Disposable Protective Cover for RF Treatment Apparatus" filed Aug. 11, 2005 and assigned Ser. No. 11/202,728, which application is a continuation of an application entitled "Cover for Electromagnetic Treatment Applicator", filed Sep. 14, 2000 now U.S. Pat. No. 6,974, 961 and assigned Ser. No. 09/661,604, which application claims the benefit of priority to a provisional application assigned Ser. No. 60/154,435, filed Sep. 17, 1999.

FIELD OF THE INVENTION

The present invention relates to electromagnetic treatment devices, and more particularly to an apparatus for covering an electromagnetic energy treatment applicator which protects the applicator from biohazards and provides selective radio frequency (RF) shielding.

BACKGROUND OF THE INVENTION

Electrotherapy includes various means of applying an electric or electromagnetic field to a wound area to facilitate growth and proliferation of new tissue, i.e., healing. In an earlier patent application filed by the present inventors, an electromagnetic treatment device is disclosed. The device includes a pulsed electromagnetic energy generator, a power level controller and one or more applicators. Each applicator is a pad comprising one or more etched copper printed circuits laminated between insulating sheets of material having high dielectric properties. Sensing units, including an electromagnetic signal strength detector and an applicator-to-patient proximity detector, are incorporated in each applicator and are in communication with the power level controller to provide for direct monitoring of te electromagnetic energy field and precise control of the treatment dosage. The applicators, which are constructed in a variety of shapes and sizes to best match the wound size and area on the patient, are placed over, under or around a bandaged wound site. Since the applicators are not disposable items, needs exist for apparatus which prevent cross-contamination between patients.

In addition, electromagnetic treatment applicators remain in direct contact with the wound site during treatment. Thus, the patient, and possibly the health care providers, are potentially exposed to the emitted radiation. Needs exist for apparatus which limit undesired exposure of the patient and health care provider to the treatment radiation.

Existing covers for radiation shielding and medical applications are unacceptable for use with electromagnetic treatment applicators, such as the one described above. Typical covers for use in medical applications are disclosed in U.S. Pat. Nos. 3,942,023, 4,605,124 and 4,715,366. Examples of other devices which provide radiation shielding are disclosed in U.S. Pat. Nos. 5,336,896 and 5,523,581. Needs exist for covers for electromagnetic treatment applicators which are cost effective, disposable and easy to use.

Citation of the above documents is not intended as a admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

SUMMARY OF THE INVENTION

It should be apparent that there exists a need for facilitating the safe and effective treatment of patients with electromagnetic energy. It is therefore a primary object of the present invention to fulfill that need by providing a cost effective, easy to use, disposable cover for use with an electromagnetic energy treatment applicator. The present cover is easy to affix to the treatment applicator, assists in easy application of the applicator to the patient, promotes the transmission of RF energy waves to the patient while blocking the propagation of those waves in any other direction, and provides biohazard shielding for protecting against the transmission of diseases between patients. Further, the cover is configured in a manner which integrates the electromagnetic properties of the cover into the circuitry for the treatment applicator, such that the applicator is not functional in the absence of the cover, thereby providing additional safeguards that the intended treatment is safe and efficacious.

More particularly, the present invention is a disposable cover for devices that are used for therapeutically treating humans with dosages of electromagnetic energy. The cover includes RF shielding material oriented toward the backside of the cover, opposite the treatment area. At least a portion of the cover which faces the treatment area is constructed solely from non-shielding material. Securing means, such as adhesive strips or interlocking edges, are provided for securing the applicator inside the cover and closing off any leaks. The cover also includes portions which wrap around the cord leading from the applicator to the generating unit.

In use, an electromagnetic treatment applicator is inserted into the present cover and positioned over the area to be treated, with the RF non-shielding (RF transmissive) portion or window of the cover overlying the treatment area. In one embodiment, the dimensions of the window are formed by removing selected strips from the outer surface of the cover. Once assembled, the applicator/cover combination forms a closely matched and tuned network for effecting a highly efficient RF output. When activated, the generated electromagnetic energy only exits the cover through the RF transmissive portion or window, thereby preventing exposure of the patient or caregiver to potentially harmful radiation.

The present invention has immediate commercial market potential in the field of chronic wound healing. Beyond that immediate market, the present invention may also be utilized in other treatment fields where increasing the rate of growth and proliferation of human or other living cells is essential, including the treatment of burns and surgically implanted skin or soft tissue grafts, sports and rehabilitation medicine, post surgical repair, and neuronal/brain/spinal injury repair and regeneration. In addition to the medical treatment of soft tissue, the present invention has applications in the field of laboratory growth/manufacturing of skin grafts to be sold and use in various surgical settings, veterinary medicine and related fields.

These and further and other objects and features of the invention are apparent in the disclosure, which includes the above and ongoing written specification, with the drawings.

BRIEF DESCRIPTION OF THE DRAWINGS

FIG. 3 is a plan view of the disposable cover with mating interlocking structures.

DETAILED DESCRIPTION OF THE INVENTION

Figure 1:
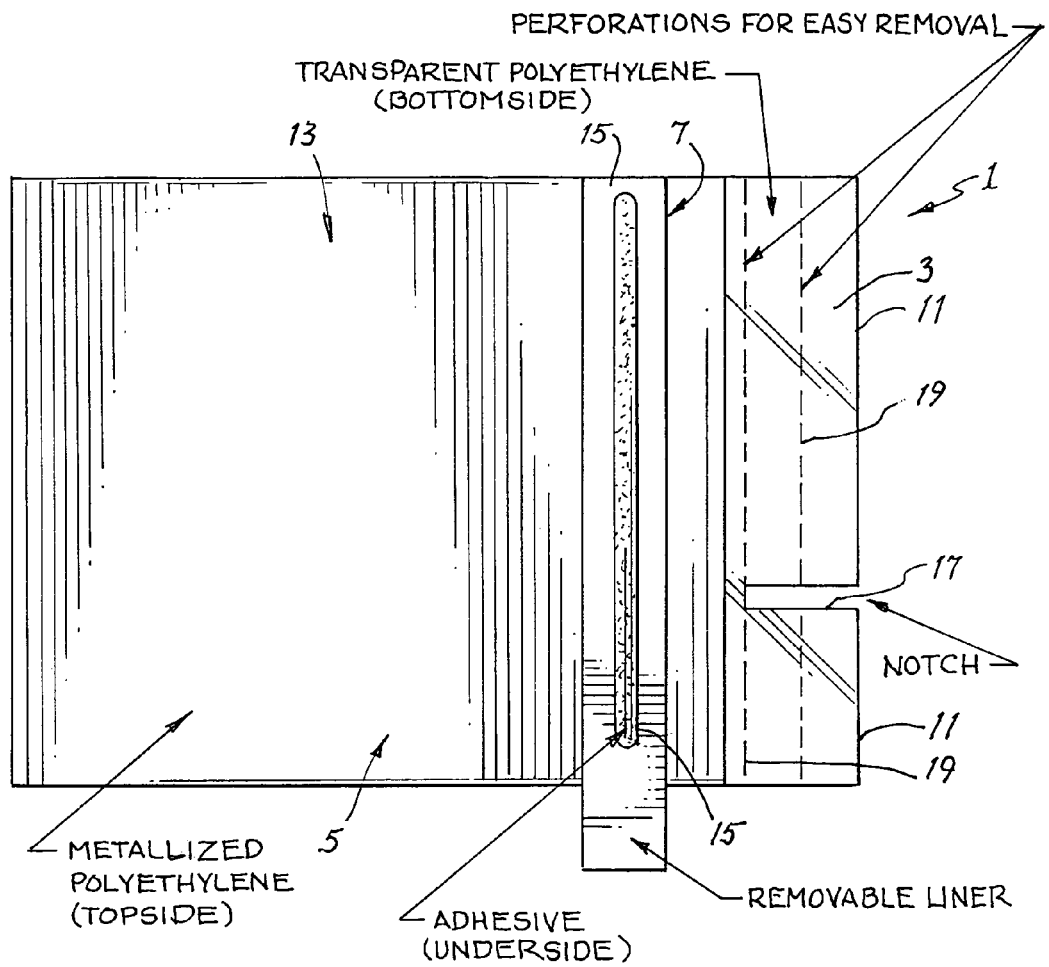
FIG. 1 is a plan view of the disposable cover.

Referring now to the drawings, where like elements are designated by like reference numerals throughout, FIG. 1 shows an apparatus, more fully described below, for covering an electromagnetic energy treatment applicator. Apparatus 1 includes a front sheet 3 and a back sheet 5. Edges of the sheets 3, 5 are sealed or otherwise connected to form a pouch-like structure with an open end 7 for receiving an applicator (not shown). In alternative embodiments, the apparatus 1 is made from a single sheet, which is folded and sealed such that it has an open end 7. The front sheet 3 (which faces the treatment area) is preferably made, at least partially, of a non-shielding material, such as transparent polyethylene. The back sheet 5 (which faces opposite, or away from, the treatment area) is preferably constructed entirely from shielding material, such as metallized polyethylene, thereby ensuring the blockage of unintended RF transmissions in nontreatment directions. One or more light adhesive strips are located along the outer surface of the front sheet 3 for affixing the cover 1 to a bandage. Preferably, the front sheet 3 of the cover 1 has a patch of adhesive at its center for securing the applicator over the treatment area. The selected adhesive is of low bonding force enabling easy separation from the mating surface.

As shown in FIG. 1, a tab portion 11 extends from the front sheet 3. After the applicator is inserted in the cover 1 through its open end 7, tab portion 11 is folded over such that it overlies a section of the outer surface 13 of the back sheet 5. In one embodiment, an adhesive strip 15 is provided along the outer surface 13 of the back sheet 5 for securing the tab portion 11 in its folded position. In another embodiment, tab portion 11 has a permanent adhesive strip which preferably runs the length of the unsealed end. It should be understood that other attachment means for securing the tab portion 11 in its folded position are contemplated by the present invention. Preferably, tab portion 11 includes a semi-circular notch 17 or other similar opening or spacing which allows a coaxial cable to protrude therethrough when the cover 1 is sealed. Tab portion 11 further includes perforations 19, preferably provided along the length of the tab portion 11, for enabling easy removal. It should also be understood that, in yet another embodiment, tab portion 11 consists of interlocking means to connect it to a second tab portion extending along the top of front sheet 3. (FIG. 3)

For additional biohazard protection, the tab portion 11 is extended, thereby allowing the tab portion 11 to be wrapped around the cable. In such embodiments, no notch is required. Rather, the extended tab portion 11 is wrapped around the cable and secured thereto with adhesive located along a surface of the tab portion. The tab portion is also secured to the back sheet 5 to seal off entry to the interior of the cover 1 where the applicator is located.

It should be understood that the tab portion 11 can extend from the back sheet 5, as opposed to the front sheet 3, or from both the back sheet 5 and the front sheet 3 without departing from the scope of the present invention. Other means for sealing off the open end of the cover 1, including, but not limited to, mating tabs, interlocking strips, or other fastening means, are also contemplated by the present invention.

In an alternative preferred embodiment, shown in FIG. 3, tab portions extend from both the front sheet 3 and the back sheet 5. Mating interlocking means 12 are located along each tab portion 11.

In its preferred form, the cover 1 is rectangular in shape and approximately 10 inches by 12 inches in size. The thickness of the cover 1 is approximately $1/100$ of an inch. At least the outer surface of the cover 1 is waterproof and bacterial resistant, and is designed to be placed directly on the patient or on top of any standard dressings used over the area to be treated.

As described earlier, the cover 1 is composed of a combination of two types of materials—one selected for its properties of resistance to transmission of RF waves and one selected for its ability to be mechanically joined to the first material. Both materials are preferably also good barriers to moisture absorption, thereby preventing biohazards from coming in contact with the applicator surfaces. The RF shielding material prevents emission from the applicator in any direction other than that to be focused at the wound site. The shielding enables the use of the electromagnetic treatment device while being compliant with standards for transmission of radio frequency and other forms of electromagnetic energy.

In its simplest form, the front sheet 3 is made of a non-shielding material and the back sheet 5 is made of a shielding material. It should be understood, however, that variations of this embodiment are also contemplated by the present invention. For example, the entire cover can be constructed of RF shielding material except for a window over the treatment zone (the treatment zone is characterized as the area above the applicator transmitting antenna). In an alternative embodiment, the entire cover, or a portion thereof, can be constructed of non-shielding material, with strips of shielding material adhered thereto. For example, RF shielding material perforated in concentric circles, or other shapes, are bonded to the outer surface of the transparent material. In such embodiments, the window over the treatment zone can be variable in size, with the user able to peel off certain shielding strips to match the transmission region to that of the wound to be treated. Other variations are also considered within the scope of the present invention.

Figure 2:
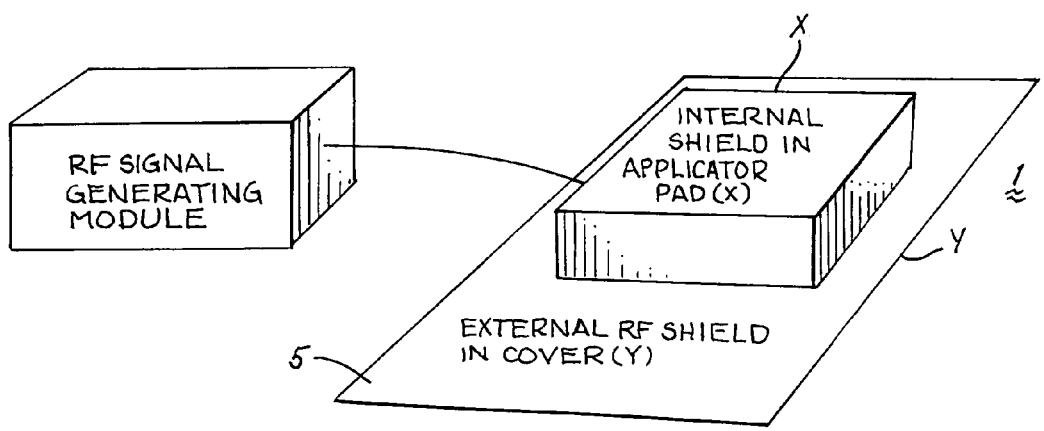
FIG. 2 is a block diagram showing how the cover is configured to integrate its electromagnetic properties into the circuitry of the applicator.

In preferred embodiments, proper placement of the cover 1 over the applicator is required for the device to operate. Preferably, the applicator (such as the one disclosed in the present applicants' earlier patent application) incorporates RF shielding material as a capacitor which is part of the electronic tuning of the applicator. Without the cover, the applicator cannot be tuned, thus the electromagnetic energy treatment device will detect a fault and will not operate. In one embodiment, as shown in FIG. 2, cover 1 includes a shielded side which conveys a particular capacitance upon the circuitry enclosed within the applicator. When the requisite capacitance is present, the applicator sends an appropriate voltage signal to a previously described power generator device (described in earlier application filed by inventors), enabling the device. In the absence of the cover conveying the requisite capacitance, the voltage signal remains outside of a predetermined range and the power generating device is disabled. In other words, the RF shielding provided by the cover acts as an additional source of capacitance (Y) which changes the final capacitance of system (Z). The RF generating system is adjusted such that it is only operable when the capacitance is within range provided by the capacitance within the internal applicator pad shield circuitry (X) plus the capacitance (Y) provided by the cover.

The present invention is operated by placing the treatment applicator into the cover through its open end, with the treatment side of the applicator oriented towards the front sheet and the coaxial cable of the applicator protruding through the open end. A permanent adhesive peel strip (which is located on the tab portion or the back sheet) is removed, exposing the adhesive. Tab portion is folded over the end of the applicator, with the semi-circular cutout notch aligned with the coaxial cable. The tab portion is then pressed against the back sheet to fully close the cover.

Where the cover includes an extended tab portion, there is no semi-circular cable cutout. Rather the extended tab portion is folded over and wrapped around the coaxial cable and bonded together to form a biohazard barrier. For further securement, a portion of the tab portion also adheres to the back sheet.

Next, the peel strip material is removed from the outer surface of the front sheet to expose a low bonding force adhesive. The covered applicator is aligned with the wound site. Indicia, such as printed designs, may be located on the outer surface of the front sheet for facilitating proper alignment. The cover is then adhered to the bandaged wound site, thus ensuring proper location of the applicator to the wound site. The adhesive is not permanent and can easily be pulled away from the bandaged site.

Following treatment, the cover is removed from the applicator and properly disposed. Preferably, removal of the cover involves the following steps. First, the cover is gripped at the two corners away from the end with the protruding coaxial cable. Pulling the corners in opposite directions causes the cover to tear at the center. As the tear clears the cover can be removed from the applicator and disposed. For embodiments including the extended tab portion, the user continues the tear the cover past the intersection of the applicator and cable until the cover can be removed.

From the foregoing, it will be appreciated by those skilled in the art that the present invention provides a particularly effective and advantageous method of and apparatus for overcoming many of the limitations associated with the treatment of patients using electromagnetic energy. It will also be readily appreciated by one with ordinary skill in the art to use the method and apparatus of the present invention in other applications, such as veterinary applications.

Although certain presently preferred embodiments of the present invention have been specifically described herein, it will be apparent to those skilled in the art to which the invention pertains that variations and modifications of the various embodiments shown and described herein may be made without departing from the spirit and scope of the invention.

The invention claimed is:

1. A system comprising:
a radio frequency (RF) generator;
an electromagnetic treatment applicator attached to the RF generator with a cable; and
a disposable cover configured to cover the electromagnetic treatment applicator, the disposable cover having an open end, a front side, a back side opposite the front side, wherein the open end is configured to permit insertion and removal of the electromagnetic treatment applicator into and out of the disposable cover, wherein at least a portion of the back side of the disposable cover includes an RF shielding material having a capacitance, wherein the electromagnetic treatment applicator is configured to detect the presence of the disposable cover based on the capacitance.

2. The system of claim 1, wherein the electromagnetic treatment applicator is configured to send a signal to the RF generator to enable the RF generator when the presence of the disposable cover is detected.

3. The system of claim 2, wherein the RF generator is disenable when the signal is not sent by electromagnetic treatment applicator.

4. The system of claim 1, wherein the back side is formed entirely of RF shielding material.

5. The system of claim 4, wherein the RF shielding material is metallized polyethylene.

6. The system of claim 1, wherein at least a portion of the front side of the disposable cover is formed of an RF non-shielding material, and wherein the backside of the disposable cover is formed entirely of an RF shielding material.

7. The system of claim 1, wherein the disposable cover includes a tab portion configured to close the open end when the electromagnetic treatment applicator is inserted into the disposable cover.

8. A system comprising:
a radio frequency (RF) generator;
an electromagnetic treatment applicator attached to the RF generator with a cable, the electromagnetic treatment applicator having a first side and an opposite second side, wherein the first side is to be positioned adjacent a treatment area; and
a disposable cover configured to cover the electromagnetic treatment applicator, the disposable cover having an open end, a front side, a back side, wherein the open end is configured to permit insertion and removal of the electromagnetic treatment applicator into and out of the disposable cover, wherein the front side is configured to be positioned adjacent the first side of the electromagnetic treatment applicator when the electromagnetic treatment applicator is inserted into the disposable cover, and wherein the back side is configured to be positioned adjacent the second side of the electromagnetic treatment applicator when the electromagnetic treatment applicator is inserted into the disposable cover, wherein at least a portion of the front side of the disposable cover is formed of an RF non-shielding material, and wherein the backside of the disposable cover is formed entirely of an RF shielding material.

9. The system of claim 8, wherein at least a portion of the back side of the disposable cover includes an RF shielding material having a capacitance, wherein the electromagnetic treatment applicator is configured to detect the presence of the disposable cover based on the capacitance.

10. The system of claim 9, wherein the electromagnetic treatment applicator is configured to send a signal to the RF generator to enable the RF generator when the presence of the disposable cover is detected.

11. The system of claim 10, wherein the RF generator is disenable when the signal is not sent by electromagnetic treatment applicator.

12. The system of claim 9, wherein the back side is formed entirely of RF shielding material.

13. The system of claim 12, wherein the RF shielding material is metallized polyethylene.

14. The system of claim 8, wherein the disposable cover includes a tab portion configured to close the open end when the electromagnetic treatment applicator is inserted into the disposable cover.

15. The system of claim 14, wherein the tab portion includes an opening for the cable.

16. The system of claim 14, wherein the tab portion includes fasteners to close the open end.

17. A method of using an electromagnetic treatment device, the electromagnetic treatment device having a radio frequency (RF) generator and an electromagnetic treatment applicator attached to the RF generator with a cable, the electromagnetic treatment applicator having a first side and a second side opposite the first side, the method comprising:

inserting the electromagnetic treatment applicator into a disposable cover, the disposable cover having a front side and a back side opposite the front side, wherein at least a portion of the front side includes an RF non-shielding material, wherein at least a portion of the back side includes an RF shielding material, wherein the electromagnetic treatment applicator is inserted to have the front side of the disposable cover adjacent to the first side of the electromagnetic treatment applicator and the back side of the disposable cover adjacent to the second side of the electromagnetic treatment applicator;

positioning the electromagnetic treatment applicator with the first side of the electromagnetic treatment applicator adjacent to a treatment area, wherein RF energy is applied to the treatment area through the first side of the electromagnetic applicator, wherein the RF energy is transmitted through the portion of the front side of the disposable cover that includes RF non-shielding material, and wherein the RF energy is blocked by the portion of the back side of the disposable cover that includes RF shielding material;

removing the electromagnetic treatment applicator from the disposable cover after the RF energy has been applied to the treatment area; and disposing the disposable cover after removing the electromagnetic treatment applicator from the disposable cover.

18. The method of claim 17, wherein the electromagnetic treatment applicator is configured to detect the presence of the disposable cover based on the capacitance, wherein the electromagnetic treatment applicator is configured to send a signal to the RF generator to enable the RF generator when the presence of the disposable cover is detected, and wherein the RF generator is disenable when the signal is not sent by electromagnetic treatment applicator.

19. The method of claim 17, wherein the back side is formed entirely of RF shielding material.

* * * * *